US006248375B1

(12) United States Patent
Gilles et al.

(10) Patent No.: US 6,248,375 B1
(45) Date of Patent: Jun. 19, 2001

(54) DIABETIC NUTRITIONALS AND METHOD OF USING

(75) Inventors: Stephanie M. Gilles, Hilliard; Bryan W. Wolf, Johnstown, both of OH (US); Bradley A. Zinker, Vernon Hills, IL (US); Keith A. Garleb, Powell, OH (US); Joseph E. Walton, Westerville, OH (US); Sue E. Nicholson, Worthington, OH (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/524,445

(22) Filed: Mar. 14, 2000

(51) Int. Cl.⁷ .............................. A23L 1/302; A23L 1/304; A23L 1/0522; A23L 1/09

(52) U.S. Cl. ................... 426/72; 426/2; 426/74; 426/103; 426/548; 426/661; 426/800; 426/808; 426/810; 424/439; 514/60; 514/866

(58) Field of Search ................... 426/72, 74, 2, 426/800, 810, 808, 548, 661, 103; 424/439; 514/60, 866

(56) References Cited

U.S. PATENT DOCUMENTS

| 5,470,839 | * | 11/1995 | Laughlin et al. | 426/810 |
| 5,605,893 | * | 2/1997 | Kaufman | 426/808 |
| 5,776,887 | * | 7/1998 | Wilbert et al. | 514/2 |

* cited by examiner

Primary Examiner—Helen Pratt
(74) Attorney, Agent, or Firm—Nickki L. Parlet

(57) ABSTRACT

The present invention is directed to solid matrix nutritionals designed for the person with diabetes. The carbohydrate system of this invention utilizes a source of fructose in combination with at least one nonabsorbent carbohydrate to achieve the same effect of prior art complex multi-component carbohydrate systems. This carbohydrate system has the added benefits of tasting good and can be incorporated into solid matrix nutritionals. The solid matrix nutritionals may also include a source of dietary fiber and a source of indigestible oligosaccharides. The solid matrix nutritionals may be administered to a diabetic in the form of cereal, bread, cookies, muffins, bagels, biscuits, crackers and bars. Particularly, the present invention is directed to a nutritional bar designed for the person with diabetes which incorporates the carbohydrate system. The present invention is also directed to a method of delivering nutrients to a person with diabetes by feeding the solid matrix nutritionals which incorporates the carbohydrate system.

19 Claims, No Drawings

DIABETIC NUTRITIONALS AND METHOD OF USING

CROSS REFERENCE

This application is related to the Carbohydrate System and a Method for Providing Nutririon to a Diabetic, application Ser. No. 09/524,716, filed concurrently herewith by Wolf et al., the contents of which are hereby incorporated by reference.

The instant invention relates to solid matrix nutritionals designed for a person with diabetes. The matrix nutritional comprises a two component carbohydrate system which blunts the postprandial glycemic response. The solid matrix nutritional may be administered to a diabetic in the form of cereal, bread, cookies, muffins, bagels, biscuits, crackers and bars. Particularly, the present invention is directed to a nutritional bar designed for the person with diabetes which incorporates the two component carbohydrate system. The invention further relates to a method of delivering nutrition to an individual diabetes.

BACKGROUND

Primary treatment for glucose intolerance is strict adherence to a diet which minimizes postprandial glucose response, and in many cases, use of medications (insulin or oral hypoglycemic agents).

Before 1921, starvation was the only recognized treatment of diabetes mellitus (DM). Since the discovery of exogenous insulin, diet has been a major focus of therapy. Recommendations for the distribution of calories from carbohydrate and fat have shifted over the last 75 years. Based on the opinions of the time, the best mix to promote metabolic control are listed in Table 1 below.

TABLE 1

History of Recommended Caloric Distribution of Persons with DM

| Year | Carbohydrate (%) | Protein (%) | Fat (%) |
|---|---|---|---|
| 1921 | 20 | 10 | 70 |
| 1950 | 40 | 20 | 40 |
| 1971 | 45 | 20 | 35 |
| 1986 | 50–60 | 12–20 | 30 |
| 1994 | * | 10–20 | *^ |

*based on nutritional assessment
^<10% saturated fat

Early recommendations limited dietary carbohydrate, because glycemic control was generally better with this type of regimen. However, over the years researchers found that low-carbohydrate, high-fat diets were associated with dyslipidemias and cardiovascular disease, because most high-fat diets consumed in industrialized countries were high in saturated fat. In 1950, the American Diabetes Association (ADA) recommended increasing the proportion of calories provided by carbohydrate to lower cardiovascular risk. While the risk for cardiovascular disease might be diminished by this strategy, research demonstrated that not all persons with DM respond favorably from the standpoint of metabolic control. In addition, the saturated fat being consumed continued to contribute to cardiovascular risk. The ADA's recommendation to restrict total fat, without regard to type of fat was challenged in the late 1980s by investigators and participants in the National Institutes of Health (NIH) Consensus Development Conference on diet and exercise in patients with type 2 DM. The recommendation of a carbohydrate-rich diet for all persons with DM also was criticized because the theory that high-carbohydrate diets improve glycemic control and insulin sensitivity was not accepted due to inconclusive evidence. The NIH Conference led to the investigation of other dietary therapies, which resulted in a radical change in the 1994 ADA nutrition recommendations. The new ADA guidelines emphasize individualization of diet strategies. The purpose is to achieve optimal glycemic and metabolic control by varying the proportion of calories provided by the macro nutrients. The proportion selected depends on goals for glycemic control, dietary preferences and response to the diet.

The American Diabetes Association (ADA) currently recommends a diet in which protein is the same as that for the general population and accounts for 10% to 20% of total calories. With protein contributing 10% to 20% of the total calories, 80% to 90% of the total calories remains to be distributed between carbohydrate and fat. The carbohydrate/fat mix is individualized according to dietary preference, treatment goals, metabolic control and the presence of other medical conditions. However, the ADA does make a recommendation for the various types of fat in the diet. Specifically, saturated fat should contribute less than 10% of total calories, and polyunsaturated fat contributing no more than 10% of total calories. The remainder of fat calories should come from monounsaturated fat and the daily intake of cholesterol should be limited to less than 300 mg. The recommendation for fiber intake is the same as for the general public with approximately 20 to 35 g/day of dietary fiber from a variety of food sources. The micro nutrient requirements of otherwise healthy persons with DM will likely be met by consuming the amounts suggested by the RDIs. The relationship of the minerals chromium and magnesium to management of DM has been the focus of much research. Individuals considered at risk for micro nutrient deficiencies should be evaluated to determine if supplementation is necessary.

Products designed as nutritionals for the person with diabetes are commercially available. These nutritional products are typically liquids or in a solid form such as nutritional bars and baked goods. The solid forms have an advantage over liquid nutritionals as the solid form does not pass through the stomach as rapidly as a liquid. Therefore, the fat content of the solid forms may be decreased as the fat is not required to slow down the passage of nutrients from the stomach. Additionally, the commercial nutritional bars incorporate various complex multi-component carbohydrate systems which are digested at different rates thereby blunting the absorption curve of carbohydrates after a meal.

Ensure® Glucerna® Nutritional Bars (Ross Products Division of Abbott Laboratories, Columbus Ohio) is a complete, balanced nutritional designed specifically for people with diabetes. Soy protein, calcium caseinate and corn protein make up 14% of total calories as protein; high fructose corn syrup, honey, microencapsulated guar gum, crisp rice, maltodextrin, soy polysaccharide, sucrose, glycerin, polydextrose and oat bran make up 61% of total calories as carbohydrate; and partially hydrogenated soy and cottonseed oils, high oleic safflower oil, canola oil and soy lecithin make up 25% of total calories as fat. Microencapsulated guar gum, soy polysaccharide, cocoa powder and oat bran contribute 4 g total dietary fiber per 1.34 oz bar. One bar provides at least 15% of the RDIs for 24 key vitamins and minerals. The product also contains the ultra trace minerals selenium, chromium and molybdenum.

Choice dm® Bar (Mead Johnson & Company, Evansville, Ind.) is a nutritional bar with fiber, antioxidants and 24 essential vitamins and minerals for people with diabetes.

Calcium caseinate, soy protein isolate, whey protein concentrate, toasted soybeans, soy nuggets (soy protein isolate, rice flour, malt, salt) and peanut butter make up 17.1% of total calories as protein; lactose, fructose, sugar, dextrose, honey, maltodextrin, rice syrup, sorbitol and peanut flour make up 54.3% of total calories as carbohydrate; and palm kernel oil and canola oil make up 28.9% of total calories as fat.

Gluc-O-Bar® (Amoun Pharmaceutical Industries Co., Westmont, Ill.) is a medical food designed for the use in the dietary management of diabetes. Soy protein isolate, nonfat dry milk and peanut flour make up 23% of total calories as protein: maltodextrin, cornstarch, sorbitol, maltitol, polydextrose and crisp rice make up 70% of total calories as carbohydrate; and chocolate creme (chocolate liquor, partially hydrogenated soybean and cottonseed oil, soy bean oil) and canola oil make up 7% of total calories as fat.

U.S. Pat. No. 4,921,877 to Cashmere et al. describes a nutritionally complete liquid formula with 20 to 37% of total caloric value from a carbohydrate blend which consists of corn starch, fructose and soy polysaccharide; 40 to 60% of total caloric value from a fat blend with less than 10% of total calories derived from saturated fatty acids, up to 10% of total calories from polyunsaturated fatty acids and the balance of fat calories from monounsaturated fatty acids; 8 to 25% of total caloric value is protein; at least the minimum US RDA for vitamins and minerals; effective amounts of ultra trace minerals chromium, selenium and molybdenum; and effective amounts of carnitine, taurine and inositol for the dietary management of persons with glucose intolerance.

U.S. Pat. No. 5,545,414 to Behr et al. describes a nutritional bar which contains protein, fat and carbohydrate. A primary component of the carbohydrate system is a zein encapsulated dietary fiber known to lower serum cholesterol in humans.

U.S. Pat. No. 5,776,887 to Wibert et al. describes a nutritional composition for the dietary management of diabetics containing 1 to 50% total calories protein; 0 to 45% total calories fat, 5 to 90% total calories carbohydrate system and fiber. The carbohydrate system contains a rapidly absorbed fraction such as glucose or sucrose, a moderately absorbed fraction such as certain cooked starches or fructose and a slowly absorbed fraction such as raw corn starch.

U.S. Pat. No. 5,470,839 to Laughlin et al. describes a composition and method for providing nutrition to a diabetic patient. The composition contains a protein source, a carbohydrate source including a slowly digested high amylose starch, a fat source that includes medium chain triglycerides and has an n–6:n–3 ratio of not more than 10.

U.S. Pat. No. 4,871,557 to Linscott describes a granola bar with supplemental dietary fiber which is added to the granola bar in the form of compressed flakes.

U.S. Pat. No. 5,843,921 and 5,605,893 both to Kaufaman describe a therapeutic food composition and a method of using the therapeutic food composition to diminish fluctuations in blood sugar levels and prevent hypoglycemic episodes. The composition includes slowly absorbed complex carbohydrate, more rapidly absorbed complex carbohydrate, protein, fat and a least one sweetening agent.

The prior art describes complex multi-component carbohydrate systems which blunt the glycemic response by requiring three or more sources of carbohydrate that are absorbed at different rates. These complex multi-component carbohydrate systems possess physical characteristics which make incorporation of the multi-component carbohydrate systems into solid matrix nutritionals difficult. Additionally, these complex carbohydrate systems often have unacceptable organoleptic characteristics and are not well tolerated. For example, guar gum functions to provide viscosity in the stomach thereby slowing the release of nutrients to the small intestine. Guar gum is encapsulated to protect the soluble fiber from moisture which results in an unacceptably hard bar. However, upon chewing, the encapsulated guar gum packs in-between the teeth, swells in the mouth and catches in the throat when swallowed.

Additionally, the amounts of the multi-component carbohydrate systems required to obtain the desired effect are often not well tolerated. For example, increased levels of fermentable fiber can lead to unacceptable bloating and flatulence in many persons.

Thus, a need has developed in the art for a simple two component carbohydrate system which acts to blunt the absorption curve of carbohydrates after a meal, is well tolerated and is easily incorporated into a solid matrix nutritional. Particularly, a need has developed in the art for a good tasting nutritional bar which provides nutrients to a person with diabetes.

SUMMARY OF THE INVENTION

The present invention is directed to solid matrix nutritionals designed for the person with diabetes that solves a number of problems associated with the prior art. Since the aim of diabetic therapy is to prevent large fluctuations in blood glucose throughout the day, diabetics are advised to select carbohydrate foods that minimize the postprandial blood glucose excursions. The prior art teaches that a complex multi-component carbohydrate system should be used. These systems incorporate differing carbohydrate sources that are digested and absorbed at differing rates. While theses systems produce improved blood glucose levels after a meal, they are difficult to manufacture in volume. The inherent variability of natural material such as raw corn starch further exacerbates manufacturing difficulties.

A new two component carbohydrate system has been developed for solid matrix nutritionals that are designed to be consumed by diabetics. This two component system is fructose or a source of fructose and at least one nonabsorbent carbohydrate. This two component system has unexpectedly been discovered to produce a glycemic response comparable to that of the more complex multi-component carbohydrate systems of the prior art. Further, this two component system is much simpler to incorporate into solid matrix nutritionals than those of the prior art and tastes good. The solid matrix nutritionals may be in the form of cereal, bread, cookies, muffins, bagels, biscuits, crackers and bars.

The solid matrix nutritional may also include dietary fiber and indigestible oligosaccharides, thereby increasing fecal bulk, modifying the transit time of nutrients through the gut and providing nutrients to the beneficial microflora of the gut which all contribute to a healthy gut.

Particularly, the present invention is directed to a nutritional bar designed for the person with diabetes which incorporates the two component carbohydrate system.

The present invention is also directed to a method of delivering nutrients to a person with diabetes by feeding a solid matrix nutritional, such as a bar or baked good, which incorporates the two component carbohydrate system of the instant invention.

DETAILED DESCRIPTION

As used in this application:

a. "glycemic index" (GI) is calculated by dividing the blood glucose incremental area under the curve (AUC) of the test food by the blood glucose AUC of the reference food and multiplying by 100, where the carbohydrate content of test and reference foods are the same. The reference food is typically glucose or white bread which has the standard GI of 100.

b. the term "total dietary fiber" or "dietary fiber" refers to the sum of the soluble and insoluble fibers. These food components are not broken down by the alimentary enzymes of humans to small molecules which are absorbed into the bloodstream.

c. "soluble" and "insoluble" dietary fiber is determined using American Association of Cereal Chemists (AACC) Method 32-07. A "soluble" dietary fiber source refers to a fiber source in which at least 60% of the dietary fiber is soluble dietary fiber as determined by AACC Method 32-07, and an "insoluble" dietary fiber source refers to a fiber source in which at least 60% of the total dietary fiber is insoluble dietary fiber as determined by AACC Method 32-07.

d. "fermentable" and "non-fermentable" dietary fiber is determined by the procedure described in "Fermentability of Various Fiber Sources by Human Fecal Bacteria In Vitro", at AMERICAN JOURNAL CLINICAL NUTRITION, 1991; 53:1418–1424. This procedure is also described in U.S. Pat. No. 5,085,883 to Garleb et al., the teachings of both of which are incorporated herein by reference. "Non-fermentable" dietary fiber refers to dietary fibers which have a relatively low fermentability of less than 40% by weight, preferably less than 30% by weight, and the term "fermentable" dietary fiber refers to dietary fibers which have a relatively high fermentability of greater than 60% by weight, preferably greater than 70% by weight.

e. the term "indigestible oligosaccharide" refers to a small carbohydrate moiety with a degree of polymerization less than or equal to about 20 and/or a molecular weight less than or equal to about 3,600, that is resistant to endogenous digestion in the human upper digestive tract.

f. the term "nonabsorbent carbohydrates" refers to a carbohydrate moiety with a degree of polymerization greater than about 20 and/or a molecular weight greater than about 3,600, that is resistant to endogenous digestion in the human upper digestive tract. Nonabsorbent carbohydrates possess many of the characteristics of total dietary fiber. However, they are not quantifiable by the MCC Method 32-07 for fiber and consequently they are not included in total dietary fiber values of the instant invention.

g. the term "total calories" refers to the total caloric content of a definitive weight of the finished nutritional product.

h. the term "Reference Daily Intakes or RDI" refers to a set of dietary references based on the Recommended Dietary Allowances for essential vitamins and minerals. The Recommended Dietary Allowances are a set of estimated nutrient allowances established by the National Academy of Sciences, which are updated periodically to reflect current scientific knowledge.

i. the terms "fructose" and "source of fructose" are used interchangeably and refer to the actual fructose content in a carbohydrate source.

j. "sucrose free" refers to sucrose levels less than 0.5 wt/wt % of the solid matrix nutritional.

An aspect of the instant invention are solid matrix nutritionals designed to incorporate a two component carbohydrate system which blunts the glycemic response like the complex multi-component carbohydrate systems of the prior art. The solid matrix nutritionals of this invention are essentially sucrose free and are designed to be used as a meal replacement or nutritional supplement for persons with DM. The solid matrix nutritionals comprise a protein source, a fat source, a carbohydrate source, vitamins, and minerals in amounts sufficient to supplement a diabetic's normal diet. Such amounts are well known by those skilled in the art and can be readily calculated when preparing such products.

Although not intended to limit the invention in any manner, but to merely serve as a general guideline, a solid matrix nutritional of this invention will typically provide the caloric distribution described in Table 2.

TABLE 2

Solid Matrix Nutritional Component Ranges

| Component | Target (% Calories) | Preferred (% Calories) | More preferred (% Calories) |
|---|---|---|---|
| Protein | 10–25 | 10–20 | 15–20 |
| Fat | <30 | 10–30 | 20–30 |
| Carbohydrate | 45–90 | 50–80 | 50–65 |

The first component of the solid matrix nutritionals of this invention is a two component carbohydrate system. The two component carbohydrate system of the instant invention comprises a source of fructose and at least one nonabsorbent carbohydrate. Component ranges for the two component carbohydrate system are described in Table 3 on a dry matter basis.

TABLE 3

Carbohydrate System Ranges (wt/wt % of carbohydrate system)

| Component | Range (wt/wt %) | Preferred (wt/wt %) | More Preferred (wt/wt %) |
|---|---|---|---|
| fructose | 65–100 | 70–90 | 70–80 |
| nonabsorbent carbohydrate | 0–35 | 10–30 | 20–30 |

The first component of the two component carbohydrate system of the instant invention is a source of fructose. The fructose source provides sweetness and has a good glycemic index (GI=30). Any fructose source suitable for human consumption may be utilized in the instant invention. Examples of typical fructose sources include high fructose corn syrup, honey and liquid and powder fructose. As indicated in Table 3, the typical amount of fructose in the two component carbohydrate system is from about 65 wt/wt % to about 100 wt/wt % of the two component carbohydrate system, preferably from about 70 wt/wt % to about 90 wt/wt % of the two component carbohydrate system, more preferably from about 70 wt/wt % to about 80 wt/wt % of the two component carbohydrate system.

Fructose is found naturally in fruits and honey. More typically, commercially available fructose is produced by enzymatic conversion of saccharides to fructose. The fructose content of various sources is listed in Table 4.

TABLE 4

Carbohydrate profile of several fructose sources*

| % dry basis | fructose | high fructose corn syrup (representative profiles) | | honey |
|---|---|---|---|---|
| fructose | 99.5 | 42 | 55 | 49 |
| dextrose | 0.5 | 52 | 41 | 40 |
| maltose | 0 | 3 | 2 | 9 |
| higher saccharides | 0 | 3 | 2 | 2 |

*Fructose and corn syrup data from Cargill, Minneapolis, Minnesota product information sheets, honey values from National Honey Board, San Francisco, California Commercial high fructose corn syrup is available at various levels of fructose. The high fructose corn syrup profiles listed in Table 4 represent two commercially available fructose sources, with fructose at 42% and 55% of the corn syrup, respectively. Any reference in this application to a quantity of fructose should be understood as referring to the actual fructose content within the carbohydrate source. For example, 100 gm of the honey in Table 4 would provide 49 gm of fructose. One skilled in the art can readily calculate how much of a carbohydrate source should be added to the solid matrix nutritional product in order to deliver the desired amount of fructose.

Commercial sources for the fructose are readily available and known to one practicing the art. For example, various high fructose corn syrups are available from Cargil in Minneapolis, Minn. Fructose is available from A. E. Staley in Decatur Illinois and honey is available from De Zaan Inc. in Fort Lee, N.J.

The second component of the two component carbohydrate system is nonabsorbent carbohydrates which comprises less than or equal to about 35 wt/wt % of the two component carbohydrate system, preferably from about 10 wt/wt % to about 30 wt/wt % of the two component carbohydrate system, more preferably from about 20 wt/wt % to about 30 wt/wt % of the two component carbohydrate system.

Examples of nonabsorbent carbohydrate sources of the instant invention typically include chemically modified starches such as Fibersol 2(E) and inulin.

Nonabsorbent carbohydrates possess many of the characteristics of fibers but are not quantified by the AACC method as total dietary fiber. Chemical modification of starch can ultimately affect its rate and extent of digestion in the small intestine. Partial hydrolysis of starch using acid and heat results in molecular rearrangement of the starch molecule such that alpha and beta-(1,2) and -(1,3) linkages are formed in addition to reconfiguration of existing alpha-(1,4) and -(1,6) bonds into beta bonds. For example, corn starch treated with hydrochloric acid, amylase and heat produces a low molecular weight indigestible dextrin (distributed by Matsutani Chemical Industry, Hyogo Japan under the product name Fibersol 2(E)) with a slow rate of fermentation. Therefore, the nonabsorbent carbohydrate is more likely to reach the lower part of the large intestine and be utilized by the indigenous microbiota.

Inulin is usually purified from plants such as chicory, Jerusalem artichoke, leek and asparagus. Various procedures for extracting the inulin have been reported. Usually the steps include chopping up the plant and extraction of the inulin.

Commercial sources of nonabsorbent carbohydrates are readily available and known to one practicing the art. For example, Fibersol 2(E) is available from Matsutani Chemical Industry, Hyogo Japan while inulin is available from Rhone-Poulenc, Inc, Cranbury, N.J.

The second component of the solid matrix nutritional products of this invention is protein. The proteins that may be utilized in the solid matrix nutritional products of the invention include any proteins suitable for human consumption. Such proteins are well known by those skilled in the art and can be readily selected when preparing such products. Examples of suitable proteins that may be utilized typically include casein, whey, milk protein, soy, pea, rice, corn, hydrolyzed protein and mixtures thereof. As indicated in Table 2, the typical amount of protein in the nutritional bar is from about 10% to about 25% of total calories, preferably from about 10% to about 20% of total calories, more preferably from about 15% to about 20% of total calories.

The preferred protein component typically comprises about 100 wt/wt % of the protein component as soy protein.

Commercial sources for the proteins listed above are readily available and known to one practicing the art. For example, caseinates, whey, hydrolyzed caseinates, hydrolyzed whey and milk proteins are available from New Zealand Milk Products of Santa Rosa, Calif. Soy and hydrolyzed soy proteins are available from Protein Technologies International of Saint Louis, Mo. Pea protein is available from Feinkost Ingredients Company of Lodi, Ohio. Rice protein is available from California Natural Products of Lathrop, Calif. Corn protein is available from EnerGenetics Inc. of Keokuk, Iowa.

The third component of the solid matrix nutritional of this invention is the fat. As noted above, the fat source of this invention will typically provide less than about 30% of the total calories, preferably about 10% to about 30% of the total calories, more preferably from about 20% to about 30% of the total calories. The fat source for the present invention may be any fat source or blend of fat sources which provides the desired levels of saturated (less than 10% kcal), polyunsaturated (up to 10% kcal) and monounsaturated fatty acids (10% to 15% kcal). Examples of food grade fats are well known in the art and typically include soy oil, olive oil, marine oil, sunflower oil, high oleic sunflower oil, safflower oil, high oleic safflower oil, fractionated coconut oil (MCToil), cottonseed oil, corn oil, canola oil, palm oil, palm kernel oil and mixtures thereof.

The preferred fat component typically comprises about 66 wt/wt % of the fat as high oleic safflower oil, about 27 wt/wt % of the fat as canola oil and about 7 wt/wt % of the fat as soy lecithin.

Numerous commercial sources for the fats listed above are readily available and known to one practicing the art. For example, soy and canola oils are available from Archer Daniels Midland of Decatur, Ill. Corn, coconut, palm and palm kernel oils are available from Premier Edible Oils Corporation of Portland, Oreg. Fractionated coconut oil (MCT oil) is available from Henkel Corporation of LaGrange, Ill. High oleic safflower and high oleic sunflower oils are available from SVO Specialty Products of Eastlake, Ohio. Marine oil is available from Mochida International of Tokyo, Japan. Olive oil is available from Anglia Oils of North Humberside, United Kingdom. Sunflower and cottonseed oils are available from Cargil of Minneapolis, Minn. Safflower oil is available from California Oils Corporation of Richmond, Calif.

Optional ingredients, dietary fiber and indigestible oligosaccharides, may be incorporated into the solid matrix nutritional. Typically for every gram of dietary fiber and indigestible oligosaccharide added to the formulation, a gram of the two component carbohydrate system is removed. Typically up to about 25% of the two component carbohydrate system may be removed and replaced with dietary fiber and indigestible oligosaccharide.

An optional component of the solid matrix nutritional is dietary fiber which comprises less than or equal to about 30 wt/wt % of the solid matrix nutritional, preferably from about 5 wt/wt % to about 20 wt/wt % of the solid matrix nutritional, more preferably from about 10 wt/wt % to about 20 wt/wt % of the solid matrix nutritional.

Examples of dietary fiber sources of the instant invention typically include gum arabic, carboxymethylcellulose, guar gum, gellan gum, gum acacia, citrus pectin, low and high methoxy pectin, modified cellulose, oat and barley glucans, carrageenan, psyllium, soy polysaccharide, oat hull fiber, pea hull fiber, soy hull fiber, soy cotyledon fiber, sugar beet fiber, cellulose, corn bran and hydrolyzed forms of the listed fibers, encapsulated forms of the listed fibers and any combination thereof.

Numerous types of dietary fibers are known and available to one practicing the art. Fibers differ significantly in their chemical composition and physical structure and therefore their physiological functions. The dietary fiber sources utilized in this invention can be characterized by the terms solubility and fermentability. With regard to solubility, fiber can be divided into soluble and insoluble types and fiber sources differ in the amount of soluble and insoluble fiber they contain.

The preferred dietary fiber component comprises about 62 wt/wt % of the fiber component as soy polysaccharide, about 21 wt/wt % of the fiber component as encapsulated guar gum and about 17 wt/wt % of the fiber component as microcrystalline cellulose.

Representative of soluble dietary fiber sources are gum arabic, sodium carboxymethylcellulose, guar gum, gellan gum, citrus pectin, low and high methoxy pectin, oat and barley glucans, carrageenan and psyllium. Numerous commercial sources of soluble dietary fibers are readily available and known to one practicing the art. For example, gum arabic, hydrolyzed carboxymethylcellulose, guar gum, pectin and the low and high methoxy pectins are available from TIC Gums, Inc. of Belcamp, Maryland. The oat and barley glucans are available from Mountain Lake Specialty Ingredients, Inc. of Omaha, Neb. Psyllium is available from the Meer Corporation of North Bergen, N.J. while the carrageenan is available from FMC Corporation of Philadelphia, Pa.

Many of the soluble dietary fibers are difficult to incorporate into a solid matrix nutritionals due to their affinity to bind moisture which results in a hard food product. Encapsulation of the soluble fiber facilitates their incorporation into a solid matrix nutritional. U.S. Pat. No. 5,545,414 teaches how to encapsulate dietary fiber with zein and is hereby incorporated by reference.

Representative of the insoluble dietary fibers are oat hull fiber, pea hull fiber, soy hull fiber, soy cotyledon fiber, sugar beet fiber, cellulose and corn bran. Numerous sources for the insoluble dietary fibers are readily available and known to one practicing the art. For example, the corn bran is available from Quaker Oats of Chicago, Ill.; oat hull fiber from Canadian Harvest of Cambridge, Minn.; pea hull fiber from Woodstone Foods of Winnipeg, Canada; soy hull fiber and oat hull fiber from The Fibrad Group of LaVale, Md.; soy cotyledon fiber from Protein Technologies International of St. Louis, Mo.; sugar beet fiber from Delta Fiber Foods of Minneapolis, Minn. and cellulose from the James River Corp. of Saddle Brook, N.J.

Dietary fiber can also be divided into fermentable and non-fermentable types. This property of fiber is the capacity to be fermented by the anaerobic bacteria present in the human large bowel. Dietary fibers vary significantly in their fermentability.

Representative of fermentable dietary fiber sources are gum arabic and guar gum. Commercial sources of fermentable dietary fibers are readily available and known to one practicing the art. For example, gum arabic and guar gum are available from TIC Gums, Inc. of Belcamp, Md.

Representative of non-fermentable dietary fiber sources are carboxymethylcellulose (CMC), psyllium, oat hull fiber and corn bran. Numerous commercial sources of non-fermentable dietary fibers are readily available and known to one practicing the art. For example, carboxymethylcellulose is available from TIC Gums, Inc. of Belcamp, Md. The corn bran is available from Quaker Oats of Chicago, Ill. while the oat hull fiber is available from Canadian Harvest of Cambridge, Minn. Psyllium is available from the Meer Corporation of North Bergen, N.J.

A second optional component of the solid matrix nutritional is indigestible oligosaccharides which comprises less than or equal to about 2.5 wt/wt % of the solid matrix nutritional.

Examples of indigestible oligosaccharides sources of the instant invention typically include fructooligosaccharides (FOS), xylooligosaccharides(XOS), alpha glucooligosaccharides(GOS), trans galactosyl oligosaccharides(TOS), soybean oligosaccharides, lactosucrose, hydrolyzed inulin and polydextrose.

An indigestible oligosaccharide, such as fructooligosaccharide(FOS), is rapidly and extensively fermented to short chain fatty acids by anaerobic microorganisms that inhabit the large bowel increasing cell proliferation in the proximal colonic epithelial mucosa. Further, FOS is a preferential energy source for most Bifidobacterium species but it is not utilized by potentially pathogenic organisms such as *Clostridium perfingens, C. difficile*, or *E. coli*. Thus, the addition of FOS to the nutritional products of the present invention selects for beneficial bacteria, such as bifidobacteria, but against potential pathogens, such as *Clostridium difficile* and putrefactive bacteria.

The preferred indigestible oligosaccharide component typically comprises about 100 wt/wt % of the indigestible oligosaccharide as FOS.

Numerous commercial sources of indigestible oligosaccharides are readily available and known to one practicing the art. For example, FOS is available from Golden Technologies Company of Golden, Colo. and XOS is available from Suntory Limited of Osaka, Japan. GOS is available from Solabia, Pantin Cedex, France. TOS is available from Yakult Honsha Co., Tokyo, Japan. Soybean oligosaccharide is available from Calpis Corporation distributed by Ajinomoto U.S.A. Inc., Teaneck, N.J. Hydrolyzed inulin is available from Rhone-Poulenc, Inc, Cranbury, N.J. while polydextrose is available from A. E. Staley in Decatur Ill.

The solid matrix nutritional compositions of the invention desirably contain vitamins and minerals. Vitamins and minerals are understood to be essential in the daily diet. Those skilled in the art appreciate that minimum requirements have been established for certain vitamins and minerals that are known to be necessary for normal physiological function. Practitioners also understand that appropriate additional amounts of vitamin and mineral ingredients need to be provided to nutritional compositions to compensate for some loss during processing and storage of such compositions. Additionally, the practitioner understands that certain micronutrients may have potential benefit for people with diabetes such as chromium, carnitine, taurine and vitamin E and that higher dietary requirements may exist for certain micronutrients such as ascorbic acid due to higher turnover in people with type 2 diabetes.

An example of the vitamin and mineral system for a solid matrix nutritional used as a nutritional supplement typically comprises at least 10% of the RDI, preferably at least 15% of the RDI for the vitamins A, B., $B_2$, $B_6$, $B_{12}$, C, D, E, K, beta-carotene, biotin, folic acid, pantothenic acid, and niacin; the minerals calcium, magnesium, potassium, sodium, phosphorous, and chloride; the trace minerals iron, zinc, manganese, copper, and iodine; the ultra trace minerals chromium, molybdenum, selenium; and the conditionally essential nutrients such as m-inositol in from about 76 Calories to about 228 Calories.

Artificial sweeteners may also be added to the solid matrix nutritional of the instant invention to enhance the organoleptic quality of the nutritional. Examples of suitable artificial sweeteners typically include saccharine, aspartame, acesulfame K and sucralose. The solid matrix nutritional of the present invention will also desirably include a coating, flavoring and/or color to provide the nutritional products with an appealing appearance and an acceptable taste for oral consumption. For example, the nutritional bars of Examples of the Invention I and II were coated with sugar free white confectionery coating and sugar free dark confectionery coating, respectively. Examples of suitable coatings typically include compounded confectionery coating, milk chocolate coating, glazes, shellac, sugar free compounded confectionery coating, sugar free glazes and sugar free shellac. Examples of useful flavorings for the solid matrix nutritional typically include, for example, chocolate, butter pecan, strawberry, cherry, orange, peanut butter, graham and lemon.

The solid matrix nutritional of the instant invention will also desirably include ingredients which add texture to enhance the mouth feel of the solid matrix nutritional. For example, crisp rice was added at about 6.5 wt/wt % of the nutritional bar in Examples of the Invention I and II. Examples of other suitable ingredients which can add texture typically include nuts, soy nuggets, toasted oats, and fruit pieces.

The solid matrix nutritional compositions may be manufactured using cold extrusion technology as is known in the art. To prepare such compositions, typically all of the powdered components will be dry blended together. Such constituents typically include the proteins, vitamin premixes, certain carbohydrates, etc. The fat soluble components are then blended together and mixed with the powdered premix above. Finally any liquid components are then mixed into the composition, forming a plastic like composition or dough.

The process above is intended to give a plastic mass which can then be shaped, without further physical or chemical changes occurring, by the procedure known as cold forming or extrusion. In this process, the plastic mass is forced at relatively low pressure through a die which confers the desired shape and the resultant exudate is then cut off at an appropriate position to give products of the desired weight.

The mass may, for example, be forced through a die of small cross-section to form a ribbon, which is carried on a belt moving at a predetermined speed under a guillotine type cutter which operates at regular intervals. The cutter, in this case, generally consists of a sharpened blade so adjusted that it cuts through the ribbon but not the underlying belt, but may also consist of a wire. In both cases, the principle is the same; the cutting process occurs at intervals that permit the moving ribbon to be cut into pieces of equivalent weight and dimensions. Generally, this is achieved by timing the cutting strokes and maintaining belt speed at an appropriate level, but there also exist computer controlled versions of this mechanism which offer greater versatility. Alternatively, the mass may be forced through a die of large cross-section and then cut at die level into slices by an oscillating knife or wire, which drop onto a moving belt and are thus transported away. The mass may also be extruded as a sheet, which is then cut with a stamp type cutter into shapes that are appropriate, such as a cookie type cutter. Finally, the mass may also be forced into chambers on a rotary die equipped with an eccentric cam that forces the thus-formed material out of the chamber at a certain point in a rotation of the cylindrical die.

After shaping, the formed product is moved by a transfer belt or other type of material conveyor to an area where it may be further processed or simply packaged. In general, a nutritional bar of the type described would be enrobed (coated) in a material that may be chocolate, a compound chocolate coating, or some other type of coating material. In all such cases, the coating material consists of a fat that is solid at room temperature, but that is liquid at temperature in excess of e.g. 31° C., together with other materials that confer the organoleptic attributes. The coating is thus applied to the bar while molten, by permitting the bar to pass through a falling curtain of liquid coating, at the same time passing over a plate or rollers which permit coating to be applied to the under surface of the bar, and excess coating is blown off by means of air jets. Finally, the enrobed bar passes through a cooling tunnel where refrigerated air currents remove heat and cause the coating to solidify.

In contrast to the cold extrusion manufacturing process of the solid matrix nutritionals above, the solid matrix nutritionals of the instant invention may also be manufactured through a baked application or heated extrusion to produce cereals, cookies, and crackers. One knowledgeable in the arts would be able to select one of the many manufacturing processes available to produce the desired final product.

For example, a dough may be prepared by mixing the dry ingredients with liquid ingredients within a section of the extruder which has temperatures below the cooking or gelatization range of the ingredients. Alternatively, the mixing may be carried out in a batch process or in a continuous dough mixer and then fed into the extruder, depending on the final product desired. Other ingredients such as syrups or sweeteners, flavoring agents, fortification such as fibers, protein, vitamins and minerals, inlays including fruits and nuts, starch modifiers such as emulsifiers and the like may be incorporated into the dough matrix at any appropriate position along the length of the extruder barrel.

The dough then passes into the cooking or heating section of the extruder where it is heated for a time and a temperature and pressure effective to raise the temperature of the dough to temperatures sufficiently high to initiate gelatinization of the starch and denaturation of the protein. The dough is heated within the extruder to temperatures ranging from about 100° C. to about 149° C. These temperatures are necessary to begin the gelatinization and denaturation process. The temperature within the extruder is maintained sufficiently high so that the heat applied when combined with the heat resulting from the frictional energy results in the extrudate emerging from the extruder having a temperature in the range of about 100° C. to about 149° C. and pressure ranging from about 0 psig to about 500 psig.

The heated dough is discharged from the extruder into a hollow attachment. The length of the hollow attachment affects the degree of cooking which is necessary to promote flavor development; complete the gelatinization of the starch; swell the grain fractions, especially bran; enhances color development due to caramelization and maillard reaction; promotes textural enhancement and, control the loss of volatile flavor components. The length of time the dough remains in the hollow attachment is also a factor which affects the finished product characteristics. The length of the hollow attachment and the inlet feed rate of the extruder generally determines the residence time within the hollow attachment, hence, the degree of cook that is achieved. Residence time within the hollow attachment generally ranges from about 3 minutes to about 100 minutes. Typically, the length of the hollow attachment is at least 3 times the longest cross-sectional dimension of the discharge outlet of the extruder. However, the length can range from 3 times the longest cross-sectional dimension of the discharge outlet of the extruder to about 1000 times the longest cross-sectional dimension of the discharge outlet of the extruder.

The temperature and moisture of the dough is maintained as the dough passes through the hollow attachment. The product exiting the attachment generally has temperatures ranging from about 113° C. to about 135° C. and moisture level ranging from about 14% to about 22%.

Depending on the final product desired, an optional die plate containing orifices may be attached at the discharge outlet of the hollow attachment. The presence of a die plate can cause an increase in back pressure within the hollow attachment ranging from about 50 psig to about 2000 psig. The product exiting the die orifice is generally in the form of a rope which is subsequently cut into a desired size for subsequent processing. The shape of the die orifice can also vary depending on the end product desired.

The cooked mass exits the hollow attachment and is cooled to temperatures ranging from 10° C. to 93° C. In the case of a flaked product, the cooked, cooled mass is reduced to a suitable size for flaking. In cases where a die is used, pellets can be cut directly at the die face or a rope can be produced and pellets formed. The moisture content after cooling ranges from about 8% to about 20%.

The cooled mass is then shaped based on the final product desired. Typically, shaping is accomplished by a comminution mill or by other means such as shredding and grating rolls, briquetting means, pellitizers, flaking rolls and the like. The cereal or cracker shaped product can then be toasted or dried to a moisture content ranging from about 2% to about 10% depending on the final product desired.

The heated extrusion process described above may also be used to manufacture a solid matrix nutritional with cookie-like crumb structure. The partially baked dough exits the extruder at about 54° C. The dough is immediately transferred to an auger fed wire-cutting machine and cut into 1 inch diameter pieces while hot. The partially cooked dough pieces are then cooked off a microwave oven for about 70 seconds to produce distinctly leavened cookies which are brown and have a crumb-like structure and crumb-like texture.

The present invention is also directed to a method of delivering nutrients to a person with diabetes by feeding the solid matrix nutritional which incorporates the two component carbohydrate system described above.

The embodiments of the present invention may, of course, be carried out in other ways than those set forth herein without departing from the spirit and scope of the invention. The present embodiments are, therefore, to be considered in all respects as illustrative and not restrictive and that all changes and equivalents also come within the description of the present invention. The following non-limiting Examples will further illustrate the present invention.

EXAMPLE I OF THE INVENTION

The process for manufacturing 1 Kg of a lemon flavored nutritional bar of the instant invention, using the bill of materials from Table 5 is described in detail below.

TABLE 5

Listing of ingredients for lemon flavored nutritional bar

| Ingredient | Quantity per 1 kg |
|---|---|
| Sugar free white confectionery coating | 190 gm |
| Soy protein | 162.3 gm |
| Honey | 143.5 gm |
| Fibersol 2(E) | 107.9 gm |
| High fructose corn syrup | 91.5 gm |
| rice crisps | 63.5 gm |
| Soy polysaccharide | 49.1 gm |
| glycerin | 46.3 gm |
| vit/min premix | 28.2 gm |
| high oleic safflower | 27.9 gm |
| fructooligosaccharide | 21.2 gm |
| encapsulated guar gum | 16.5 gm |
| microcrystalline cellulose | 13.3 gm |
| canola | 11.7 gm |
| NA lemon creme | 10.1 gm |
| fructose | 7.8 gm |
| citric acid | 3.3 gm |
| m-inositol | 2.9 gm |
| soy lecithin | 2.8 gm | vit/min premix (per g premix): 1219 IU vitamin A, 90 IU vitamin $D_3$, 38 IU vitamin E, 19.8 mcg vitamin $K_1$, 90 mg vitamin C, 4.9 mg niacinamide, 2.33 mg calcium pantothenate, 0.187 mg folic acid, 0.377 mg thiamine mononitrate, 0.645 mg riboflavin, 0.457 mg pyridoxine hydrochloride, 2.91 mcg cyanocobalamin, 74.65 mg biotin, 2.77 mg zinc, 3.3 mg iron, 0.797 mg manganese, 0.33 mg copper, 35.1 mcg iodine, 35.9 mcg chromium, 24.3 mcg molybdenum, 24.6 mcg selenate, 227 mg calcium, 56.5 gm magnesium and 120.3 mg phosphorous The bar core is prepared by mixing a dry preblend in two stages, adding the liquid preblend followed by the canola oil. A dry preblend is prepared by mixing the required amounts of soy protein (distributed by Protein Technologies International, St. Louis, Mo.), fructooligosaccharide (distributed by Golden Technologies Company of Golden, Colorado), m-inositol and soy polysaccharide (distributed by Protein Technologies International, Louis, Mo. under the name of Fibrim 1450) for 10 minutes in a Ribbon Blender. The required amounts of the following ingredients are added to the Ribbon Blender: microcrystalline cellulose, citric acid and Fibersol 2(E) (distributed by Matsutani Chemical Industry Co., Hyogo, Japan) and mixed for an additional 20 minutes. 25 kg of the blend is removed from the bottom of the blender and added back through the top of blender and mixed for an additional 5 minutes. The dry preblend is stored in drums.

The required amount of the dry preblend above is added to a Dough Mixer along with the required amounts of lemon creme flavor (distributed by Givaudan Roure, Cincinnati, Ohio under the name of NA Lemon Creme), vit/min premix (distributed by Fortitech, Schenectady, N.Y.), microencapsulated guar gum (distributed by Coating Place, Verona, Wisconsin) and rice crisp (distributed by Weetabix, Clinton, Mass. under the name of Densifeid Crisp Rice-No sugar, salt or malt) and mixed for 200 strokes by the Dough Mixer.

The liquid preblend is prepared by adding the required amount of high fructose corn syrup (distributed by ADM Corn Processing, location under the name of cornsweet 95), honey, glycerine, crystalline fructose, high oleic safflower oil (distributed by California Oils, Richmond, Calif.) and bleached lecithin in a Hobart Mixer for 5 minutes.

All of the liquid preblend is added to the dry preblend in the Dough Mixer within the first 60 strokes. The total mixing time is set for 500 strokes. When 100 to 150 strokes is remaining, the required amount of canola oil is added to the Dough Mixer.

The mixed material is transferred from the Dough Mixer to the extruder. The extruder is adjusted to produce bar cores from 33.3 gm to 37.3 gm, the target weight is set at 35.3 gm. The extruded bar cores are conveyed through the cooling tunnel set at the target range of 8 to 12° C.

The bar cores are coated with a maltitol white confectionery coating prepared as follows. The coating is melted at a temperature range between 46–48° C. The temperature is not allowed to exceed 50° C. in the melter. Once melted, the coating is held between 46–48° C. for 30 minutes to insure destruction of all unstable crystal.

The extruded bar cores are conveyed through the enrober. The coating is applied to the bars at a temperature range between 41–48° C. The coating temperature is not allowed to exceed 50° C. in the enrober. The target percent coating is 16.3%, 19% is the maximum coating percent.

After the enrober, the coated bars are conveyed through the cooling tunnel set at 10° C., the cooling range is from 8–13° C. The bars pass through a metal detector prior to wrapping. The cooled bars are packaged in foil wrap.

EXAMPLE II OF THE INVENTION

The process for manufacturing 1 Kg of a chocolate graham flavored nutritional bar of the instant invention, using the bill of materials from Table 6 is described in detail below.

TABLE 6

Listing of ingredients for chocolate graham flavored nutritional bar

| Ingredient | Quantity per 1 kg |
|---|---|
| Sugar free dark confectionery coating | 190 gm |
| Soy protein | 162.3 gm |
| Honey | 140.9 gm |
| Fibersol 2(E) | 124.3 gm |
| High fructose corn syrup | 85.2 gm |
| Rice crisps | 63.5 gm |
| Soy polysaccharide | 49.1 gm |
| glycerin | 46.3 gm |
| vit/min premix | 28.2 gm |
| high oleic safflower | 27.9 gm |
| fructooligosaccharide | 21.2 gm |
| encapsulated guar gum | 16.5 gm |
| microcrystalline cellulose | 13.4 gm |
| canola | 11.7 gm |
| fructose | 7.8 gm |
| Art. graham cracker flavor | 3.2 gm |
| m-inositol | 2.9 gm |
| soy lecithin | 2.8 gm |
| Art. graham flavor | 1.8 gm |
| Art. creamy vanilla flavor | 0.89 gm | vit/min premix (per g premix): 1219 IU vitamin A, 90 IU vitamin $D_3$, 38 IU vitamin E, 19.8 mcg vitamin $K_1$, 90 mg vitamin C, 4.9 mg niacinamide, 2.33 mg calcium pantothenate, 0.187 mg folic acid, 0.377 mg thiamine mononitrate, 0.645 mg riboflavin, 0.457 mg pyridoxine hydrochloride, 2.91 mcg cyanocobalamin, 74.65 mg biotin, 2.77 mg zinc, 3.3 mg iron, 0.797 mg manganese, 0.33 mg copper, 35.1 mcg iodine, 35.9 mcg chromium, 24.3 mcg molybdenum, 24.6 mcg selenate, 227 mg calcium, 56.5 gm magnesium and 120.3 mg phosphorous The bar core is prepared by mixing a dry preblend in two stages, adding the liquid preblend followed by the canola oil. A dry preblend is prepared by mixing the required amounts of soy protein (distributed by Protein Technologies International, St. Louis, Mo.), fructooligosaccharide (distributed by Golden Technologies Company of Golden, Colo.), inositol and soy polysaccharide (distributed by Protein Technologies International, Louis, Mo. under the name of Fibrim 1450) for 10 minutes in a Ribbon Blender. The required amounts of the following ingredients are added to the Ribbon Blender: microcrystalline cellulose and Fibersol 2(E) (distributed by Matsutani Chemical Industry Co., Hyogo) and mixed for an additional 20 minutes. 25 kg of the blend is removed from the bottom of the blender and added back through the top of blender and mixed for an additional 5 minutes. The dry preblend is stored in drums.

The required amount of the dry preblend above is added to a Dough Mixer along with the required amounts of vit/min premix (distributed by Fortitech, Schenectady, N.Y.), microencapsulated guar gum (distributed by Coating Place, Verona, Wis.) and crisp rice (distributed by Weetabix, Clinton, Mass. under the name of Densifeid Crisp Rice-No sugar, salt or malt) and mixed for 200 strokes by the Dough Mixer.

The liquid preblend is prepared by adding the required amount of high fructose corn syrup (distributed by ADM Corn Processing, location under the name of cornsweet 95), honey, glycerine, crystalline fructose, high oleic safflower oil (distributed by California Oils, Richmond, Calif.), bleached lecithin, graham cracker flavor (distributed by Firmenich, Plainsboro, N.J. under the name of artificial graham cracker), graham flavor (distributed by SBI, Langhorn, Pa. under the name of artificial graham), and vanilla flavor (distributed by Ottens, Philadelphia, Pa. under the name of artificial creamy vanilla) in a Hobart Mixer for 5 minutes.

All of the liquid preblend is added to the dry preblend in the Dough Mixer within the first 60 strokes. The total mixing time is set for 500 strokes. When 100 to 150 strokes is remaining, the required amount of canola oil is added to the Dough Mixer.

The mixed material is transferred from the Dough Mixer to the extruder. The extruder is adjusted to produce bar cores from 33.3 gm to 37.3 gm, the target weight is set at 35.3 gm. The extruded bar cores are conveyed through the cooling tunnel set at the target range of 8 to 1 2° C.

The bar cores are coated with a maltitol chocolate confectionery (distributed by Gertrude Hawk Chocolates, Dunmore, Pa.) coating prepared as follows. The coating is melted at a temperature range between 46–48° C. The temperature is not allowed to exceed 50° C. in the melter. Once melted, the coating is held between 46–48° C. for 30 minutes to insure destruction of all unstable crystal.

The extruded bar cores are conveyed through the enrober. The coating is applied to the bars at a temperature range between 41–48° C. The coating temperature is not allowed to exceed 50° C. in the enrober. The target percent coating is 16.3%, 19% is the maximum coating percent.

After the enrober, the coated bars are conveyed through the cooling tunnel set at 10° C., the cooling range is from 8–13° C. The bars pass through a metal detector prior to wrapping. The cooled bars are packaged in foil wrapper.

A typical sugar profile of a coated 38 gm chocolate graham nutritional bar produced as described above is listed in Table 8.

TABLE 7

Sugar profile

| Sugar Components | Chocolate Graham (gm per 38 gm bar) |
| --- | --- |
| maltitiol | 3.12 |
| dextrose | 1.9 |
| fructose | 4.14 |
| sucrose | 0.18 |
| lactose | 0.29 |
| maltose | 0.57 |

Fructose and maltitol dominate the sugar profile. Dextrose is a component of the high fructose corn syrup while maltitol is a component of the sugar free dark confectionery coating. Negligible amounts of sucrose, lactose and maltose are also present.

COMPARATIVE EXAMPLE III

Many attempts were made to manufacture an acceptable bar matrix. The prototypes described below are representative of many of the processing and organoleptic challenges that had to be overcome before obtaining the acceptable bar matrix described in Examples of the Invention I and II. Bar matrix prototypes 2–5 each address the manufacturing, shelf life stability and taste issues which presented in the previous prototype.

The ingredients for each prototype are presented in the tables 8 through 12 as percent by weight of the product. Prototype number 1 served as the inventors starting point.

TABLE 8

Recipe for bar matrix prototype number 1

| Ingredient | Percent by Weight |
| --- | --- |
| Soy Protein Isolate | 15.35 |
| Encapsulated Guar Gum | 1.64 |
| Soy Polysaccharide | 5.78 |
| Oat Bran | 3 |
| Fibersol 2 (E) | 6 |
| Raw Corn Starch | 13.16 |
| Vitamin/Mineral Premix | 2.84 |
| Fructooligosaccharide Powder | 2.79 |
| myo-Inositol | 0.29 |
| Densified Crisp Rice | 6.44 |
| 55 High Fructose Corn Syrup | 11.05 |
| Glycerin, 99.7% | 4.62 |
| Fructose | 3.18 |
| High Oleic Safflower Oil | 2.8 |
| Lecithin | 0.28 |
| Art. Graham Cracker Flavor | 0.32 |
| Art. Graham Flavor | 0.18 |
| Art. Creamy Vanilla Flavor | 0.09 |
| Canola Oil | 1.19 |
| Chocolate Confectionery Coating | 19 |

The carbohydrate system of prototype 1 included the chemically modified starch Fibersol 2(E), raw corn starch, high fructose corn syrup and fructose. Prototype 1 also included the dietary fibers soy polysaccharide, encapsulated guar gum and oat bran and the indigestible oligosaccharide fructooligosaccharide. The ingredients were combined as in Example of the Invention I and II. However the final blend remained as a powder and therefor could not be extruded.

COMPARATIVE EXAMPLE IV

In response to the manufacturing issues of prototype 1, the fiber system and liquid ingredients were modified for prototype 2 to obtain a dough that could be extruded. Specifically, the levels of soy polysaccharide, Fibersol 2(E) and raw corn starch were decreased and the oat bran was removed. At the same time, the amount of corn syrup was increased and honey was added to the liquid ingredients.

TABLE 9

Recipe for bar matrix prototype number 2

| Ingredient | Percent by Weight |
| --- | --- |
| Soy Protein Isolate | 15.35 |
| Encapsulated Guar Gum | 1.64 |
| Soy Polysaccharide | 4.28 |
| Fibersol 2 (E) | 4 |
| Raw Corn Starch | 8.66 |
| Vitamin/Mineral Premix | 2.84 |
| Fructooligosaccharide Powder | 2.79 |
| myo-Inositol | 0.29 |
| Densified Crisp Rice | 6.44 |
| 90 High Fructose Corn Syrup | 12.55 |
| Glycerin, 99.7% | 4.62 |
| Honey | 9.5 |
| Fructose | 3.18 |
| High Oleic Safflower Oil | 2.8 |
| Lecithin | 0.28 |
| Art. Graham Cracker Flavor | 0.32 |
| Art. Graham Flavor | 0.18 |
| Art. Creamy Vanilla Flavor | 0.09 |
| Canola Oil | 1.19 |
| Chocolate Confectionery Coating | 19 |

The carbohydrate system of prototype 2 included the chemically modified starch Fibersol 2(E), raw corn starch, high fructose corn syrup, honey and fructose. Prototype 2 also included the dietary fibers soy polysaccharide and encapsulated guar gum and the indigestible oligosaccharide fructooligosaccharide. The ingredients were combined as in Example of the Invention I and II. The batch blended together forming a dough without the need for additional honey or high fructose corn syrup. However, the fibrous/powdery mouthfeel characteristics of the bar were unacceptable.

COMPARATIVE EXAMPLE V

Since the encapsulated guar gum contributed to the unacceptable mouth feel of prototype 2, the encapsulated guar gum was replaced with raw corn starch and oat bran in prototype number 3. Additionally, the Fibersol 2(E) was replaced with a combination of maltodextrins hydrolyzed to varying degrees.

TABLE 10

Recipe for bar matrix prototype number 3

| Ingredient | Percent by Weight |
| --- | --- |
| Soy Protein Isolate | 7.21 |
| Calcium Caseinate | 3.9 |
| Raw Corn Starch | 9.55 |
| Soy Polysaccharide | 5.77 |
| Oat Bran | 2.98 |
| Lodex 17 Maltodextrin | 3.32 |
| Maltrin 200 Maltodextrin | 2.6 |
| Vitamin/Mineral Premix | 2.82 |
| Polydextrose | 2.78 |
| myo-Inositol | 0.28 |
| Densified Crisp Rice | 6.41 |
| 55 High Fructose Corn Syrup | 14.06 |
| Honey | 9.47 |
| Glycerin, 99.7% | 4.59 |

TABLE 10-continued

Recipe for bar matrix prototype number 3

| Ingredient | Percent by Weight |
| --- | --- |
| Fructose | 0.72 |
| High Oleic Safflower Oil | 2.5 |
| Lecithin | 0.28 |
| Art. Graham Cracker Flavor | 0.32 |
| Art. Graham Flavor | 0.18 |
| Art. Creamy Vanilla Flavor | 0.09 |
| Canola Oil | 1.17 |
| Chocolate Confectionery Coating | 19 |

The carbohydrate system of prototype 3 included the raw corn starch, maltodextrin, high fructose corn syrup, honey and fructose. Prototype 3 also included the dietary fibers soy polysaccharide and oat bran and the indigestible oligosaccharide polydextrose. The ingredients were combined as in Example of the Invention I and II. The batch blended together and bars were manufactured. However, the bar texture scores for hardening became unacceptable over time.

COMPARATIVE EXAMPLE VI

The raw corn starch, maltodextrins and oat bran were removed to address the texture issues of prototype number 3. Fibersol 2(E) replaced the removed ingredients in prototype number 4.

TABLE 11

Recipe for bar matrix prototype number 4

| Ingredient | Percent by Weight |
| --- | --- |
| Soy Protein Isolate | 16.23 |
| Encapsulated Guar Gum | 1.65 |
| Fibersol 2 (E) | 12.43 |
| Soy Polysaccharide | 4.33 |
| Vitamin/Mineral Premix | 2.82 |
| Polydextrose | 2.79 |
| myo-Inositol | 0.29 |
| Densified Crisp Rice | 6.35 |
| 90 High Fructose Corn Syrup | 12.63 |
| Honey | 11.24 |
| Glycerin, 99.7% | 4.63 |
| Fructose | 0.78 |
| High Oleic Safflower Oil | 2.79 |
| Lecithin | 0.28 |
| Art. Graham Cracker Flavor | 0.32 |
| Art. Graham Flavor | 0.18 |
| Art. Creamy Vanilla Flavor | 0.09 |
| Canola Oil | 1.17 |
| Chocolate Confectionery Coating | 19 |

The carbohydrate system of prototype 4 included the chemically modified starch Fibersol 2(E), high fructose corn syrup, honey and fructose. Prototype 4 also included the dietary fibers soy polysaccharide and encapsulated guar gum and the indigestible oligosaccharide polydextrose. The ingredients were combined as in Example of the Invention I and II. While this bar had acceptable sensory and bar texture ratings through shelf life, the bar was initially too soft coming off the line and were not able to retain their required shape causing the coating to crack. Since the bar core was too soft immediately after production, the bars became deformed and the core oozed through the cracked coating.

COMPARATIVE EXAMPLE VII

The core of prototype number 4 was stiffened by removing the polydextrose and adding microcrystalline cellulose in prototype number 5. FOS was also added.

TABLE 12

Recipe for bar matrix prototype number 5

| Ingredient | Percent by Weight |
| --- | --- |
| Soy Protein Isolate | 16.23 |
| Encapsulated Guar Gum | 1.65 |
| Fibersol 2 (E) | 12.43 |
| Soy Polysaccharide | 4.91 |
| Vitamin/Mineral Premix | 2.82 |
| Fructooligosaccharide Powder | 2.12 |
| myo-Inositol | 0.29 |
| Microcrystalline Cellulose | 1.34 |
| Densified Crisp Rice | 6.35 |
| 90 High Fructose Corn Syrup | 11.38 |
| Honey | 11.24 |
| Glycerin, 99.7% | 4.63 |
| Fructose | 0.78 |
| High Oleic Safflower Oil | 2.79 |
| Lecithin | 0.28 |
| Art. Graham Cracker Flavor | 0.32 |
| Art. Graham Flavor | 0.18 |
| Art. Creamy Vanilla Flavor | 0.09 |
| Canola Oil | 1.17 |
| Chocolate Confectionery Coating | 19 |

The carbohydrate system of prototype 5 included the chemically modified starch Fibersol 2(E), high fructose corn syrup, honey and fructose. Prototype 5 also included the dietary fibers soy polysaccharide, encapsulated guar gum and microcrystalline cellulose and the indigestible oligosaccharide fructooligosaccharide. The ingredients were combined as in Example of the Invention I and II. While these prototype bars had acceptable taste and bar texture ratings over shelf life, this formulation required a much longer mix time than was acceptable. The formulations described in Example of the Invention I and II address the manufacturing issue observed in prototype number 5.

EXAMPLE OF THE INVENTION VIII

The process for manufacturing 1 Kg of a chocolate graham flavored cereal of the instant invention, using the bill of materials from Table 6 is described in detail below.

The dry ingredients are dry blended and moistened with a liquid preblend. A dry preblend is prepared by mixing the required amounts of soy protein (distributed by Protein Technologies International, St. Louis, Mo.), fructooligosaccharide (distributed by Golden Technologies Company of Golden, Colo.), m-inositol and soy polysaccharide (distributed by Protein Technologies International, Louis, Mo. under the name of Fibrim 1450) for 10 minutes in a Ribbon Blender. The required amounts of the following ingredients are added to the Ribbon Blender: microcrystalline cellulose, citric acid and Fibersol 2(E) (distributed by Matsutani Chemical Industry Co., Hyogo, Japan) and mixed for an additional 20 minutes. 25 kg of the blend is removed from the bottom of the blender and added back through the top of blender and mixed for an additional 5 minutes. The required amounts of lemon creme flavor (distributed by Givaudan Roure, Cincinnati, Ohio under the name of NA Lemon Creme), vit/min premix (distributed by Fortitech, Schenectady, N.Y.), microencapsulated guar gum (distributed by Coating Place, Verona, Wis.) and rice crisp (distributed by Weetabix, Clinton, Mass. under the name of Densifeid Crisp Rice-No sugar, salt or malt) are added and mixed an additional 10 minutes.

The liquid preblend is prepared by adding the required amount of high fructose corn syrup (distributed by ADM Corn Processing, location under the name of cornsweet 95), honey, glycerine, crystalline fructose, high oleic safflower oil (distributed by California Oils, Richmond, Calif.) and bleached lecithin in a Hobart Mixer for 5 minutes.

All of the liquid preblend is added to the dry preblend and mixed until combined. The canola oil is prepared separately by placing the canola oil in a jacketed kettle and heating to 65° C. with constant mixing.

A moderate shear screw configuration containing 5 kneading zones is placed in a 57 mm Werner & Pfleiderer twin screw extruder with a 8.9 centimeter in diameter outlet. The 10 sections are set up as follows: cold water (12° C.) is circulated through the first section containing the feed inlet; the next 5 sections are heated to 121° C. by circulating hot oil through the jackets; the 8th section contains a vent port and is not heated; and the last two sections, 9 & 10, are cooled to 90° C. using cold water in the jackets. A 1.2 meter section of 10 centimeter in diameter Teflon lined pipe (Resistoflex TFE Teflon lined pipe made by Resistoflex Div. of Crane Co.) is attached directly to the extruder outlet. A die containing 6 holes at 0.4 centimeters in diameter is attached to the end of the attachment.

The prewetted dry ingredients, at 30% moisture, are placed in an Acrison feeder and fed continuously into the hopper of the extruder at a rate of 32.8 kgm/hr.

The heated canola is pumped continuously into a port in the second section of the extruder, at a rate of 12.5 kgm/hr. Additional water is also added at the same location, to adjust the moisture of the final product. Typically, this is held at 7.3 kgm/hr. The extruder is operated at 200 rpm, which results in a torque of 30%, and a pressure of 350 psi at the end of the extruder. At this rate, the dough has a retention time of 15 minutes in the attachment and the temperature of the dough exiting the die is 115° C.

As the strands of cooked dough leave the die at the end of the attachment, they are directed over a continuous belt conveyor where they are cooled to 54° C. by pulling air through the perforated belt. The cooled strands are sized using a Conair strand cutter, by operating the feed roll at about 130 rpm and the cutter roll at about 150 rpm to form pellets about 0.635 centimeter long.

These pellets at about 18% moisture are air-cooled at 37° C. to 49° C. and fed directly to Ferrel Ross flaking rolls. Flakes are formed at about 0.025 to 0.030 of an inch thick and toasted to a moisture of 2.5% in a Jetzone oven.

We claim:
1. A nutritional bar comprising:
   a) a source of fat;
   b) a carbohydrate system consisting essentially of:
      i) a source of fructose from about 65 wt/wt % to about 100 wt/wt % of the carbohydrate system, and
      ii) at least one nonabsorbent carbohydrate source wherein said nonabsorbent carbohydrate is less than about 35 wt/wt % of the carbohydrate system; and
   c) a source of protein.

2. The nutritional bar according to claim 1 wherein said nutritional bar further comprises less than about 30 wt/wt % of the nutritional bar as dietary fiber selected from the group consisting of soluble fiber, insoluble fiber, fermentable fiber, non-fermentable fiber and mixtures thereof.

3. The nutritional bar according to claim 1 wherein said nutritional bar further comprises less than about 2.5 wt/wt % of the nutritional bar as indigestible oligosaccharides.

4. The nutritional bar according to claim 1 in which:
   a) the carbohydrate system comprises from about 45% to about 90% of the total calories of the nutritional bar;
   b) the fat source comprises less than about 30% of the total calories of the nutritional bar; and
   c) the protein source comprises from about 10% to about 25% of the total calories of the nutritional bar.

5. The nutritional bar according to claim 4 wherein the source of fat comprises from about 10% to about 30% of the total calories of the nutritional bar.

6. The nutritional bar according to claim 4 wherein the source of protein comprises from about 10% to about 20% of the total calories of the nutritional bar.

7. The nutritional bar of claim 4 wherein the carbohydrate system comprises from about 50% to about 80% of the total calories of the nutritional bar.

8. A method for providing nutrition to an individual with diabetes comprising enterally administering the nutritional bar according to claim 4.

9. The nutritional bar according to claim 1 further including at least one additional nutrient selected from the group consisting of vitamin A, vitamin B., vitamin $B_2$, vitamin $B_6$, vitamin $B_{12}$, vitamin C, vitamin D, vitamin E, vitamin K, biotin, carnitine, taurine, folic acid, pantothenic acid, niacin, choline, calcium, phosphorus, magnesium, zinc, manganese, copper, sodium, potassium, chloride, iron, selenium, chromium and molybdenum.

10. A method for providing nutrition to an individual with diabetes comprising enterally administering the nutritional bar according to claim 1.

11. A nutritional bar comprising:
   a) a carbohydrate system comprising from about 45% to about 90% of the total calories of the nutritional bar and wherein said carbohydrate system consists essentially of a source of fructose from about 65 wt/wt % to about 100 wt/wt % of the carbohydrate system and at least one nonabsorbent carbohydrate source comprising less than about 35 wt/wt % of the carbohydrate system,
   b) a fat source comprising less than about 30% of the total calories of the nutritional bar,
   c) a protein source comprising from about 10% to about 25% of the total calories of the nutritional bar,
   d) a dietary fiber source comprising less than about 30 wt/wt % of the nutritional bar; and
   e) an indigestible oligosaccharide source comprising less than about 2.5 wt/wt % of the nutritional bar.

12. The nutritional bar according to claim 11 further including at least one additional nutrient selected from the group consisting of vitamin A, vitamin B., vitamin $B_2$, vitamin $B_6$, vitamin $B_{12}$, vitamin C, vitamin D, vitamin E, vitamin K, biotin, carnitine, taurine, folic acid, pantothenic acid, niacin, choline, calcium, phosphorus, magnesium, zinc, manganese, copper, sodium, potassium, chloride, iron, selenium, chromium and molybdenum.

13. The nutritional bar according to claim 11 wherein the nutritional bar is coated with at least one coating selected from the group consisting of compounded confectionery coating, milk chocolate coating, glazes, shellac, sugar free compounded confectionery coating, sugar free glazes and sugar free shellac.

14. A method for providing nutrition to an individual with diabetes comprising enterally administering the nutritional bar according to claim 11.

15. A solid matrix nutritional comprising:
a) a source of fat;
b) a carbohydrate system which consists essentially of;
   i) a source of fructose from about 65 wt/wt % to about 100 wt/wt % of the carbohydrate system, and
   ii) at least one nonabsorbent carbohydrate less than about 35 wt/wt % of the carbohydrate system; and
c) a source of protein.

16. The solid matrix nutritional of claim 15 in a form selected from the group consisting of cereal, bread, cookies, muffins, bagels, biscuits and crackers.

17. The solid matrix nutritional according to claim 15 wherein the solid matrix nutritional is coated with at least one coating selected from the group consisting of compounded confectionery coating, milk chocolate coating, glazes, shellac, sugar free compounded confectionery coating, sugar free glazes and sugar free shellac.

18. A method for providing nutrition to an individual with diabetes comprising enterally administering the solid matrix nutritional according to claim 15.

19. A carbohydrate system suitable for incorporation into a solid matrix nutritional which consists essentially of:
a) a source of fructose from about 65 wt/wt % to about 100 wt/wt % of the carbohydrate system, and
b) at least one nonabsorbent carbohydrate wherein said nonabsorbent carbohydrate is less than about 35 wtlwt % of the carbohydrate system.

* * * * *

UNITED STATES PATENT AND TRADEMARK OFFICE
CERTIFICATE OF CORRECTION

PATENT NO. : 6,248,375 B1  
DATED : June 19, 2001  
INVENTOR(S) : Gilles et al.

Page 1 of 1

It is certified that error appears in the above-identified patent and that said Letters Patent is hereby corrected as shown below:

<u>Column 22,</u>  
Line 24, consisting of vitamin A, vitamin B delete "." insert -- $_1$ --, vitamin $B_2$, vitamin $B_6$,  
Line 53, group consisting of vitamin A, vitamin B delete "." insert -- $_1$ --, vitamin $B_2$, <u>Column 24,</u>  
Line 13, part b), nonabsorbent carbohydrate is less than about 35 wt delete "1" insert -- / -- wt Signed and Sealed this Fifth Day of November, 2002

Attest:

Attesting Officer

JAMES E. ROGAN  
*Director of the United States Patent and Trademark Office*